(12) United States Patent
Kelly (10) Patent No.: US 10,251,764 B2
(45) Date of Patent: Apr. 9, 2019

(54) UNIVERSAL CATHETER TIP AND METHODS FOR USE

(71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

(*) Notice: Subject to any disclaimer, the term of this patent is extended or adjusted under 35 U.S.C. 154(b) by 60 days.

(21) Appl. No.: 15/214,199

(22) Filed: Jul. 19, 2016

(65) Prior Publication Data

US 2017/0014252 A1 Jan. 19, 2017

Related U.S. Application Data

(60) Provisional application No. 62/312,503, filed on Mar. 24, 2016, provisional application No. 62/194,255, filed on Jul. 19, 2015.

(51) Int. Cl.
*A61B 17/34* (2006.01)
*A61M 25/00* (2006.01)
(Continued)

(52) U.S. Cl.
CPC .......... *A61F 2/95* (2013.01); *A61B 17/3417* (2013.01); *A61B 17/3468* (2013.01);
(Continued)

(58) Field of Classification Search
CPC .......... A61F 2/95; A61F 2/97; A61F 9/00736; A61B 17/3468; A61B 17/34; A61B 17/3403; A61B 17/3415; A61B 17/3417; A61B 17/3421; A61B 17/3431; A61B 17/3439; A61B 2017/347; A61B 2017/3433; A61B 2017/3445; A61B 2017/3447; A61B 2017/3449; A61B 2017/3454; A61B 2017/3456;
(Continued)

(56) References Cited

U.S. PATENT DOCUMENTS 4,682,606 A * 7/1987 DeCaprio .......... A61B 10/0266
  600/567
5,752,970 A * 5/1998 Yoon .................. A61B 17/3421
  604/167.03

(Continued)

FOREIGN PATENT DOCUMENTS

| DE | 102011121963 A1 | 6/2013 |
|---|---|---|
| EP | 1092449 A1 | 4/2001 |
| WO | 03/004084 A2 | 1/2003 |

OTHER PUBLICATIONS

International Search Report and Written Opinion for corresponding PCT Application No. PCT/US2016/042993 dated Nov. 8, 2016.

*Primary Examiner* — Darwin P Erezo
*Assistant Examiner* — Katherine H Schwiker
(74) *Attorney, Agent, or Firm* — McDonnell Boehnen Hulbert & Berghoff LLP (57) ABSTRACT

The present disclosure provides a catheter tip comprising a flexible housing comprising a cavity extending between an expandable opening arranged at a first end of the catheter tip and a second end of the catheter tip, wherein the expandable opening is configured to increase in diameter from a first position to a second position in response to application of an external force to the second end of the flexible housing.

18 Claims, 5 Drawing Sheets

(51) Int. Cl.
*A61M 25/10* (2013.01)
*A61F 2/95* (2013.01)
*A61F 2/07* (2013.01)

(52) U.S. Cl.
CPC ...... *A61M 25/008* (2013.01); *A61M 25/0068* (2013.01); *A61M 25/0069* (2013.01); *A61M 25/0074* (2013.01); *A61B 2017/3454* (2013.01); *A61F 2/07* (2013.01); *A61M 2025/0024* (2013.01); *A61M 2025/0079* (2013.01); *A61M 2025/1093* (2013.01)

(58) Field of Classification Search
CPC .... A61B 2017/346; A61B 2017/22072; A61B 2017/3425; A61B 2017/3427; A61B 2017/3429; A61B 2017/3441; A61B 2017/3464; A61B 2017/3466; A61B 2017/2808; A61B 2017/2825; A61B 2017/2829; A61B 2017/301; A61B 2017/303; A61B 2017/305; A61B 2017/505; A61B 10/06; A61M 25/0074; A61M 25/0075; A61M 25/007; A61M 25/1002; A61M 2025/0076; A61M 2025/0078; A61M 2025/0079
See application file for complete search history.

(56) References Cited

U.S. PATENT DOCUMENTS

| | | | | |
|---|---|---|---|---|
| 6,015,423 | A * | 1/2000 | Andrese | A61M 25/0068 606/194 |
| 6,508,825 | B1 * | 1/2003 | Selmon | A61M 29/02 604/104 |
| 6,939,318 | B2 * | 9/2005 | Stenzel | A61B 17/3468 604/506 |
| 8,088,154 | B2 * | 1/2012 | Hoffman | A61F 2/95 623/1.11 |
| 2002/0010476 | A1 * | 1/2002 | Mulholland | A61B 17/22031 606/108 |
| 2004/0064179 | A1 * | 4/2004 | Linder | A61F 2/013 623/1.11 |
| 2006/0184226 | A1 * | 8/2006 | Austin | A61F 2/95 623/1.11 |
| 2007/0208276 | A1 | 9/2007 | Kornkven Volk et al. | |
| 2007/0244440 | A1 * | 10/2007 | Pal | A61M 25/0074 604/164.13 |
| 2008/0161902 | A1 * | 7/2008 | Poulsen | A61F 2/95 623/1.11 |
| 2010/0204639 | A1 * | 8/2010 | Gat | A61B 18/1482 604/21 |
| 2011/0288579 | A1 * | 11/2011 | Hyodo | A61B 17/2804 606/205 |
| 2015/0250992 | A1 * | 9/2015 | Morriss | A61M 29/02 606/198 |
| 2016/0106562 | A1 * | 4/2016 | Puckett, Jr. | A61F 2/97 606/108 |

* cited by examiner

UNIVERSAL CATHETER TIP AND METHODS FOR USE

RELATED APPLICATIONS

This application claims priority to (i) U.S. Provisional Application No. 62/194,255 entitled "Universal Catheter Tip and Methods for Use," filed on Jul. 19, 2015, and (ii) U.S. Provisional Application No. 62/312,503 entitled "Universal Catheter Tip and Methods for Use," filed on Mar. 24, 2016, both of which are hereby incorporated by reference in their entirety.

BACKGROUND THE INVENTION

The current state of the art for devices that are advanced via guidewires to various arterial configurations requires a separate device for each diameter of guidewire. For example, a larger guidewire having a diameter of 0.9562 mm may be used for certain aspects of a given procedure, while a smaller guidewire having a diameter of 0.254 mm may be used for different aspects of the same procedure. Using current devices, a different catheter having a different size tip would need to be used for each guidewire size. The 0.9652 mm diameter tip cannot be used on the 0.254 mm guide wire, because there would be a ridge created that would catch on lesions that may allow blood to pass through the resulting gap and into the catheter. As a result, the various sized guidewires require a large inventory of devices that may be expensive and difficult to maintain.

SUMMARY OF THE INVENTION

The present invention is directed to a catheter tip that may be advantageously adjustable for use with guidewires of varying diameters. Such catheter tips may have a length ranging from roughly 4 cm to 60 cm and may have a diameter ranging from 4 French to 25 French depending on the device being delivered in vivo. The French size of the catheter refers to the outer diameter which is also termed the catheter's "crossing profile." Reducing the crossing profile may allow the catheter to cross narrow lesions and to enter small blood vessels. The material of the catheter tip may be flexible, kink resistant, atraumatic, and torquable. The material of the catheter tip may be silicone, polyurethane, nylon, or Pebax among other materials. Catheters and tips are also often lined by materials that are hemocompatible, lubricious, non-thrombogenic, and/or sometimes radiopaque. The inner liner materials may be polytetrafluoroethylene (PTFE), polyimide, or high density polyethylene, for example. The mechanical properties of such a catheter tip may include high burst pressure, high tensile strength and compression resistance, high modulus of elasticity and low coefficient of friction. Forming techniques for catheter tips can include coated extrusions, co-extrusions, coil-reinforced or braid-reinforced composites that may further include an inner lubricious layer, reinforcement layer and an outer jacket layer. The coil- or braid-reinforced metal layers may provide tensile strength, while the polymer layer may provide lubricity and flexibility. The catheter tips are bonded to the catheter in such a way so as to minimize risk of separation from one another during the procedure, because a tip that separates from the catheter can create a situation where blood flow is blocked to a major organ.

Thus, in a first aspect, the present invention provides a catheter tip comprising a flexible housing comprising a cavity extending between an expandable opening arranged at a first end of the catheter tip and a second end of the catheter tip, wherein the expandable opening is configured to increase in diameter from a first position to a second position in response to application of an external force to the second end of the flexible housing.

In a second aspect, the present invention provides a catheter tip comprising (a) a plurality of pivotable arms defining a cavity extending between an expandable opening arranged at a first end of the catheter tip and a second end of the catheter tip, wherein the plurality of pivotable arms are arranged to taper inwardly toward the cavity at the first end, and (b) one or more pivots arranged between an inner surface of the plurality of pivotable arms and the cavity.

In a third aspect, the present invention provides a catheter tip comprising (a) a plurality of stiff arms defining a cavity extending between an expandable opening arranged at a first end of the catheter tip and a second end of the catheter tip, wherein the plurality of stiff arms are arranged to taper inwardly toward the cavity at the first end, and (b) a stiff frame disposed within the cavity, wherein the plurality of stiff arms are moveable relative to the stiff frame from a first position in which an expandable opening has a first diameter to the second position in which the expandable opening has a second diameter that is larger than the first diameter.

In a fourth aspect, the present invention provides a method comprising: (a) applying a force to the second end of the flexible housing of the catheter tip of any one of the first aspect, the second aspect, or the third aspect, thereby increasing a diameter of the expandable opening at the first end of the catheter tip, (b) positioning a guidewire through the expandable opening, (c) removing the force from the second end of the catheter tip thereby decreasing the diameter of the expandable opening, and (d) advancing the catheter tip along the guidewire to a target lumen.

These as well as other aspects, advantages, and alternatives, will become apparent to those of ordinary skill in the art by reading the following detailed description, with reference where appropriate to the accompanying drawings.

DETAILED DESCRIPTION OF THE INVENTION

Exemplary devices and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means+/−5%.

As used herein, the "flexible housing" may be made of any material capable of being compressed and returning to the same uncompressed configuration, including, but not limited to, a polymer material, such as PLGA (poly-pactic-co-glycolic acid), PCL (poly-caprolactone) or PMMA (poly-methyl-methacrylate), rubber, or silicone.

As used herein, the "pivotable arms" may include a material having a stiffness greater than that of the flexible housing. The pivotable arms may be made of a rigid polymer or of a shape memory metal such as nitinol, as some examples.

As used herein, a "stent graft" is a tubular, radially-expandable device comprising a fluid-tight fabric supported by a stent, and may be used to bridge aneurysmal arteries. As such, the term stent graft may be used herein to include bridging stent grafts. Such stent grafts and methods for their deployment and use are known to those of skill in the art. For example, vascular sheaths can be introduced into the patient's arteries, through which items, including but not limited to, guidewires, catheters and, eventually, the stent graft, is passed.

As used herein, "stent" is typically a cylindrical frame and means any device or structure that adds rigidity, expansion force, or support to a prosthesis, while "stent graft" refers to a prosthesis comprising a stent and a graft material associated therewith that forms a fluid-tight or blood-tight lumen through at least a portion of its length. A "graft" is a cylindrical liner that may be disposed on the stent's interior, exterior or both. A wide variety of attachment mechanisms are available to join the stent and graft together, including but not limited to, sutures, adhesive bonding, heat welding, and ultrasonic welding.

The stent can be made of any suitable material, including but not limited to biocompatible metals, implantable quality stainless steel wires, nickel and titanium alloys, and biocompatible plastics. The stents can either have material properties necessary to exhibit either self-expanding or balloon-expanding characteristics.

Any suitable fluid tight, or blood tight, graft material can be used. In a preferred embodiment, the graft material is a biocompatible fabric, including but not limited to woven or knitted polyester, such as poly(ethylene terephthalate), polylactide, polyglycolide and copolymers thereof; fluorinated polymers, such as PTFE, expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. Materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. The graft material may also include extracellular matrix materials.

As used herein, a "catheter" is an apparatus configured to be connected to a deployment mechanism and to house a medical device that can be delivered over a guidewire. The catheter may include a lumen to receive a guidewire for over-the-wire guidance and may be used for delivering a stent graft or other implantable device to a target lumen. A catheter can have braided metal strands within the catheter wall to increase structural integrity. The structural elements of the catheter tip can be bonded or laser welded to the braided strands of the catheter to improve the performance characteristics of the catheter tip.

As used herein, a "guidewire" is an elongated cable comprised of various biocompatible materials that may include metals and polymers. Guidewires may be used for selecting target lumens and guiding catheters to target deployment locations. Guidewires are typically defined as wires used independently of other devices that do not come as part of an assembly.

As used herein, "lumen" refers to a passage within an arterial structure, such as the pulmonary arteries, or the passage within the tubular housings or catheters through which the guidewire may be disposed.

As used herein, "French" refers to a unit of measurement for a catheter. A round catheter of 1 French has an external diameter of ⅓ mm, and therefore the diameter of a round catheter in millimeters can be determined by dividing the French size by 3.

Figure 1:
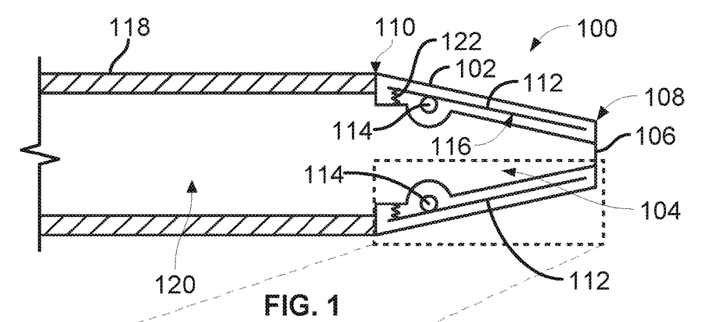
FIG. 1 illustrates a catheter tip, according to an example embodiment.

With reference to the Figures, FIG. 1 illustrates an example catheter tip 100. As shown in FIG. 1, the catheter tip 100 may include a flexible housing 102 that comprises a cavity 104 extending between an expandable opening 106 arranged at a first end 108 of the catheter tip 100 and a second end 110 of the catheter tip 100. The flexible housing 102 and/or the expandable opening 106 may be made of any material capable of being stretched and returning to the same unstretched configuration, including, but not limited to, a polymer material such as PLGA (poly-pactic-co-glycolic acid), PCL (poly-caprolactone) or PMMA (poly-methyl-methacrylate), rubber, or silicone. As such, the expandable opening 106 may be configured to increase in diameter from a first position to a second position in response to application of an external force to the second end 110 of the flexible housing 102.

Further, an inner surface of the expandable opening 106 may include ridges or teeth 105 to grip the guidewire positioned therein. The ridges or teeth 105 may comprise a different material than the expandable opening 106. For example, the ridges or teeth 105 may comprise a biocompatible metal. In another example, the ridges or teeth 105 may be the same material as the expandable opening 106. The catheter tip 100 may also include a plurality of pivotable arms 112 embedded in the flexible housing 102 extending between the first end 108 and the second end 110. Each of the plurality of pivotable arms 112 are arranged to taper inwardly toward the cavity 104 at the first end 108. The pivotable arms 112 may be made of any suitable rigid material, such as a rigid polymer or a shape memory metal, such as nitinol, as some examples.

The catheter tip 100 may also include one or more pivots 114 arranged within the housing 102 between an inner surface 116 of the plurality of pivotable arms 112 and the cavity 104. In one example, the one or more pivots 114 are arranged between the first end 108 and the second end 110 of the catheter tip 100, and are preferably arranged in a segment of the housing 102 between the second end 110 and the midpoint 111 between the first end 108 and the second end 110. The one or more pivots 114 may comprise a single ring, a discontinuous ring, a plurality of ball bearings, and/or a plurality of short shafts, as examples. In one example, each of the plurality of pivotable arms 112 has a stiffness greater than a stiffness of the flexible housing 102. In another example, there may be at least three pivotable arms 112 embedded in the flexible housing 102.

The expandable opening 106 may take a variety of forms. In one example, the expandable opening may comprise a single ring. In such an example, the expandable opening may be a part of the flexible housing 102 or be made from the same material as the flexible housing 102. In another example, the expandable opening may be a single ring that is permanently coupled to the flexible housing 102. In another example, the expandable opening 106 may comprise a discontinuous ring defined by the plurality of pivotable arms 112 at the first end 108 of the catheter tip 100. As such, the expandable opening 106 may be a meeting of the plurality of pivotable arms 112 in a first position that may be opened up to a larger diameter in a second position.

In addition, the catheter tip 100 may further include a biasing element 122 embedded within the flexible housing 102 between the second end 110 and the one or more pivots 114 and arranged to bias the plurality of pivotable arms 112 outwardly away from the cavity 114 at the second end 110 of the flexible housing 102 and inwardly towards the cavity 114 at the first end 108 of the catheter tip 100. In various embodiments, the biasing element 122 may comprise a coil spring, a torsion spring or a flat spring, as some examples. The flexible housing 102 may be molded about one or more of the pivotable arms 112, pivot 114, and biasing elements 122 such that these components are embedded in the flexible housing 102.

In one embodiment, the catheter tip 100 may further include a catheter 118 coupled to the second end 110 of the catheter tip 100. The catheter 118 may be permanently coupled to the second end 110 of the catheter tip 100, or the catheter 118 may be removeably coupled to the second end 110 of the catheter tip 100. In such an example, the catheter tip 100 may also include a guidewire-deployable device, such as an occluder, a pacemaker lead, a snare or a stent graft, positioned within a lumen 120 of the catheter 118.

Figure 2A:
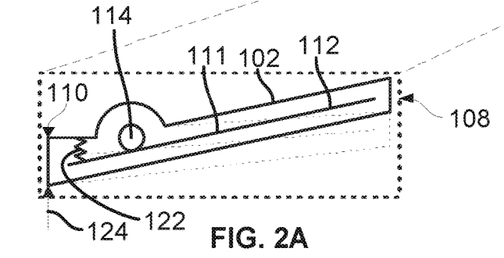
FIG. 2A is a detail view of a pivotable arm embedded in the flexible housing in an unflexed position and in a flexed position shown in dashed lines, according to the example of FIG. 1.
Figure 2B:
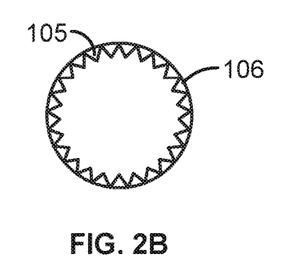
FIG. 2B is a front view of a catheter tip, according to the example of FIG. 1.

With reference to FIG. 2, a pivotable arm 112 is shown embedded in the flexible housing 102, according to an example embodiment. In this embodiment, the flexible housing 102 may be transition from an unflexed position to a flexed position by applying a force 124 to the second end 110 of the catheter tip 100. The expandable opening 106 may have a diameter in an unflexed position ranging from about 0.2032 mm to about 0.3556 mm and may have a diameter in a flexed position ranging from about 0.2286 mm to about 1.016 mm.

Figures 3, 4, 5:
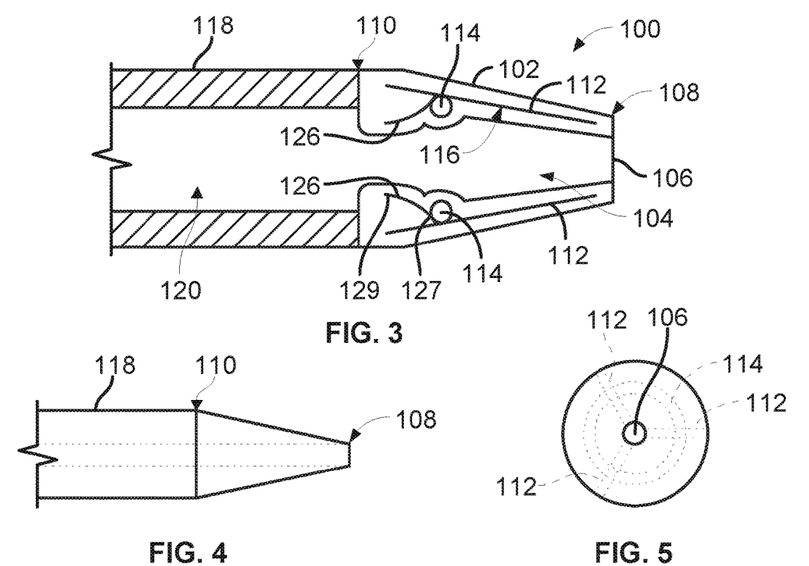
FIG. 3 illustrates a cross-sectional view of a catheter tip including a biasing arm, according to an example embodiment.
FIG. 4 illustrates a side view of a catheter tip, according to an example embodiment.
FIG. 5 illustrates a front view of the catheter tip of the example embodiment shown in FIG. 4.

Turning to FIGS. 3-7, a catheter tip 100 is shown including a plurality of biasing arms 126 each having a first end 127 coupled to at least one pivotable arm 112 near the a pivot 114 and arranged such that each biasing arm 126 is embedded in the flexible housing 102 between the cavity 104 and the plurality of pivotable arms 112. A second end 129 of each of the plurality of biasing arms 126 extends toward the second end 110 of the catheter tip 100 away from the respective pivotable arm 112 to which it is coupled and toward the cavity 104. In one example, as shown in FIG. 3, the catheter tip 100 may include one or more annular rings 128 disposed at the first end 108 of the catheter tip 100 to prevent the expandable opening 106 of the flexible housing 102 from being retracted over the plurality of pivotable arms 112.

In one example, as shown in FIGS. 4-5, the flexible housing 102 is cone-shaped. Such a configuration may be beneficial to guide the catheter tip 100 through various lumens to a target position. As shown in FIG. 5, the catheter tip 100 may include three pivotable arms 112 that pivot about a single pivot 114 that is ring-shaped. Other arrangements are possible as well.

Figure 6:
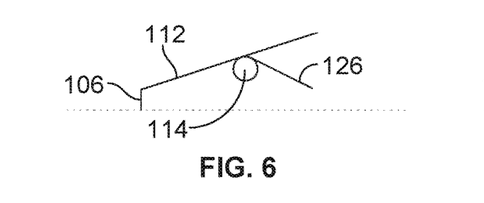
FIG. 6 illustrates a side cross-sectional view of one half of a catheter tip including a biasing arm in a relaxed position, according to an example embodiment.
Figure 7:
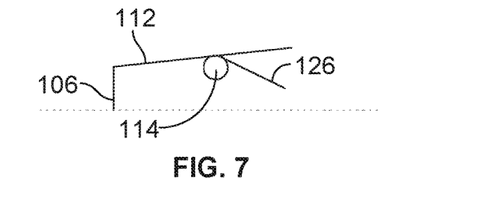
FIG. 7 illustrates a side cross-sectional view of one half of a catheter tip of the example embodiment shown in FIG. 6 in a compressed position.

FIG. 6 illustrates a cross-section of a pivotable arm 112 and biasing arm 126 of one half of the catheter tip 100 of FIGS. 3-5 with the biasing arm 126 in a relaxed position, and FIG. 7 illustrates a cross-section of a pivotable arm 112 and biasing arm 126 of one half of the catheter tip 100 of FIGS. 3-5 with the biasing arm 126 in a compressed position. As shown in FIGS. 6 and 7, when the biasing arm 126 is in the relaxed position, the expandable opening 106 has a smaller diameter than when the biasing arm 126 is in the compressed position.

In operation, a user may pinch or compress the flexible housing 102, causing the pivotable arms 112 to rotate about the one or more pivots 114 and to flex outwardly in a direction away from the cavity 104 (see FIG. 7), thereby increasing the diameter of the expandable opening 106. Once a guidewire has been disposed through the flexed opening 106, the user may release the compression on the flexible housing and the pivotable arms 112 may return the flexible housing 102 to the unflexed position (see FIG. 6). In practice, the expandable opening 106 of the flexible housing 102 may apply enough pressure on the guidewire to seal the opening 106 of the catheter tip 100 about the guidewire 150 to minimize the entry of bodily fluids into the cavity 104 of the catheter tip 100. In addition, the expandable opening 106 is configured to permit the guidewire to slide back and forth within the catheter tip 100 without binding. In one particular example, the expandable opening 106 may include a lubricating material to reduce any friction between the guidewire 150 and the expandable opening 106.

An example method may include (a) applying a compressive force to the second end 110 of the catheter tip 100 according to any one of the example embodiments described above, thereby increasing a diameter of the expandable opening 106 at the first end 108 of the catheter tip 100, (b) positioning a guidewire 150 through the expandable opening 106, (c) removing the compressive force from the second end 110 of the catheter tip 100 thereby decreasing the diameter of the expandable opening 106, and (d) advancing the catheter tip 100 along the guidewire 150 to a target lumen. In another embodiment, the catheter tip 100 is coupled to a catheter 118 with a stent graft positioned within a lumen 120 of the catheter 118. In such an embodiment, the method may further include deploying the stent graft from the lumen 120 of the catheter 118 into the target lumen.

Figure 8:
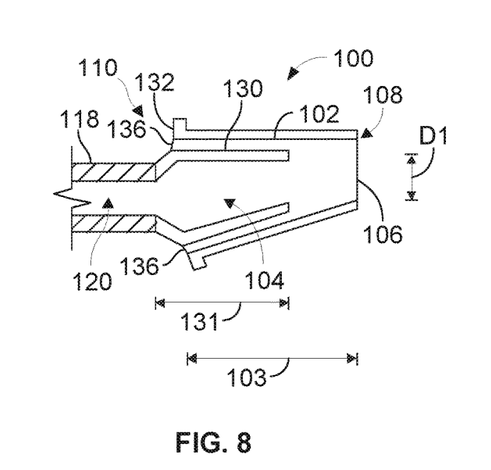
FIG. 8 illustrates a side cross-sectional view of a catheter tip in a first position, according to an example embodiment.
Figure 9:
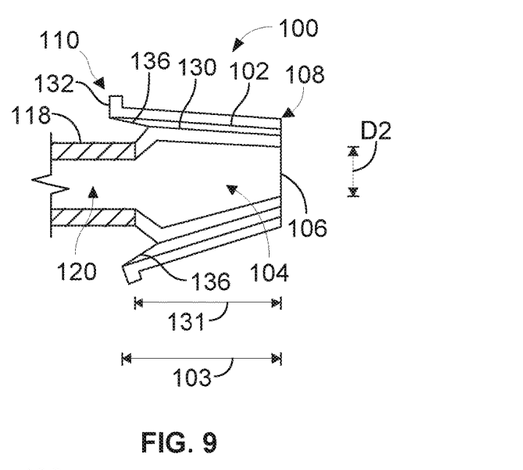
FIG. 9 illustrates a side cross-sectional view of the catheter tip of FIG. 8 in a second position.

With respect to FIGS. 8-9, a catheter tip 100 is shown according to a further example embodiment that may include a flexible housing 102 that is conical in shape that comprises a cavity 104 extending between an expandable opening 106 arranged at a first end 108 of the catheter tip and a second end 110 of the catheter tip 100. The expandable opening 106 is configured to increase in diameter from a first position to a second position in response to application of a force to the flexible housing 102.

In one example, the catheter tip 100 may include a stiff frame 130 disposed within the cavity 104. The stiff frame 130 may be conical, longitudinal, or ring-shaped, as examples. In one example as shown in FIGS. 8-9, a length of the stiff frame 131 is less than a length of the flexible housing 103. The flexible housing 102 is moveable relative to the stiff frame 130 from a first position (see FIG. 8) in which the expandable opening 106 has a first diameter to a second position (see FIG. 9) in which the expandable opening 106 has a second diameter that is larger than the first diameter. The first diameter D1 of the expandable opening 106 may range from about 0.2032 mm to about 0.3556 mm, and the second diameter D2 of the expandable opening 106 may range from about 0.2286 mm to about 1.016 mm. The technical effect of the first diameter is that a seal between the guidewire and the expandable opening 106 may be obtained, while still permitting movement of the guidewire 150 therethrough.

Figures 10, 11:
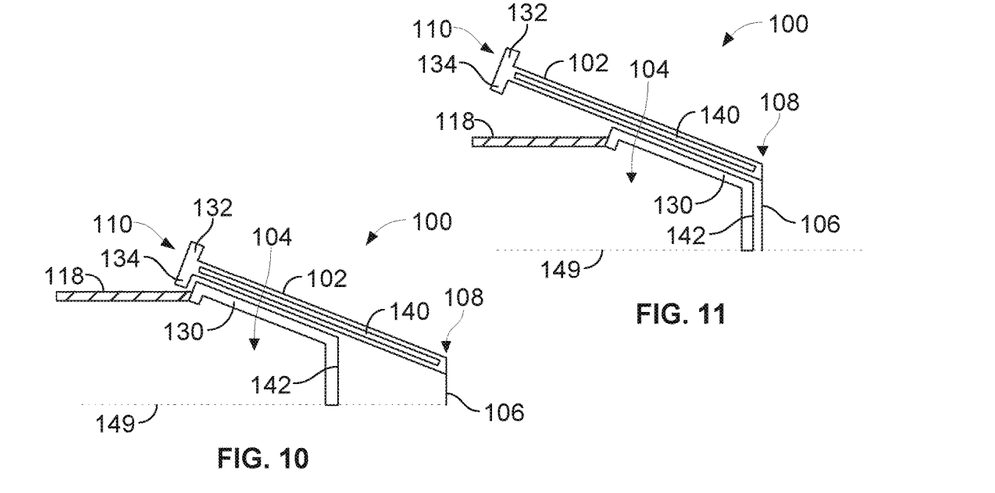
FIG. 10 illustrates a side cross-sectional view of one half of a catheter tip including a plurality of stiff arms in a first position, according to an example embodiment.
FIG. 11 illustrates a side cross-sectional view of one half of the catheter tip of the example embodiment shown in FIG. 10 in a second position.

In one example, as shown in FIGS. 8-11, the catheter tip 100 may include a first flange 132 coupled to the second end 110 of the flexible housing 102 and extending radially outward from the flexible housing 102. In operation, the first flange 132 may be used by a user as a grip surface to retract the flexible housing 102 from the first position (see FIGS. 8, 10) to the second position (see FIG. 9, 11). Further, as shown in FIGS. 10-11, the catheter tip 100 may include a second flange 134 coupled to the second end 110 of the flexible housing 102 and extending radially inward from the flexible housing 102. In operation, the second flange 134 may be used to prevent the flexible housing 102 from being separated from the stiff frame 130. The catheter tip 100 can also be flexible such that when it is pulled to the second position it curves around the outer surface of the catheter 118 in such a way as to minimize the overall crossing profile of the catheter 118, as discussed in additional detail below.

Further, the catheter tip 100 may also include a first biasing element 136, such as a coiled spring, having a first end and a second end. The first end of the biasing element 136 may be coupled to the second end 110 of the catheter tip 100, and the second end of the biasing element 136 may be coupled to the stiff frame 130. In operation, such a biasing element 136 may assist in advancing the flexible housing 102 back toward the first position. In addition, the catheter tip 100 may also include a second biasing element (not shown), such as a Z-spring, embedded in the flexible housing 102. Such a Z-spring may have an expanded condition in the first unflexed position of the housing 102, and a contracted position in the second flexed position of the housing 102. As such, the Z-spring may assist in advancing the flexible housing 102 back toward the first position.

In one embodiment, the catheter tip 100 may further include a catheter 118 coupled to the second end 110 of the catheter tip 100. The catheter 118 may be permanently coupled to the second end 100 of the catheter tip 100, or the catheter 118 may be removeably coupled to the second end 100 of the catheter tip 100. In such an example, the catheter 118 may also include a guidewire-deployable device, such as an occluder, a pacemaker lead, a snare or a stent graft, positioned within a lumen 120 of the catheter 118.

As shown in the example embodiment of FIGS. 10-11, the catheter tip 100 may alternatively include a plurality of stiff arms 140 embedded in the flexible housing 102 that extend between the first end 108 and the second end 110 of the catheter tip 100. The plurality of stiff arms 140 may be substantial similar to the plurality of pivotable arms 112 described above, but arranged to slide with respect to the stiff frame 130 instead of rotating about the pivot 114 as described above. In such an example, the plurality of stiff arms 140 may be arranged to form a cone shape in the first position (see FIG. 10) and to spread apart in the second position (see FIG. 11). In one example, the plurality of stiff arms 140 comprises at least three stiff arms. In another example, the catheter tip 100 includes one or more annular rings 128 disposed at the first end 108 of the catheter tip 100 to prevent the expandable opening 106 of the flexible housing 102 from being retracted over the stiff frame 130. In yet another example, a first end of the stiff frame 130 has a fixed opening 142 that corresponds to the second diameter of the expandable opening 106 of the flexible housing 102.

Figures 12, 13:
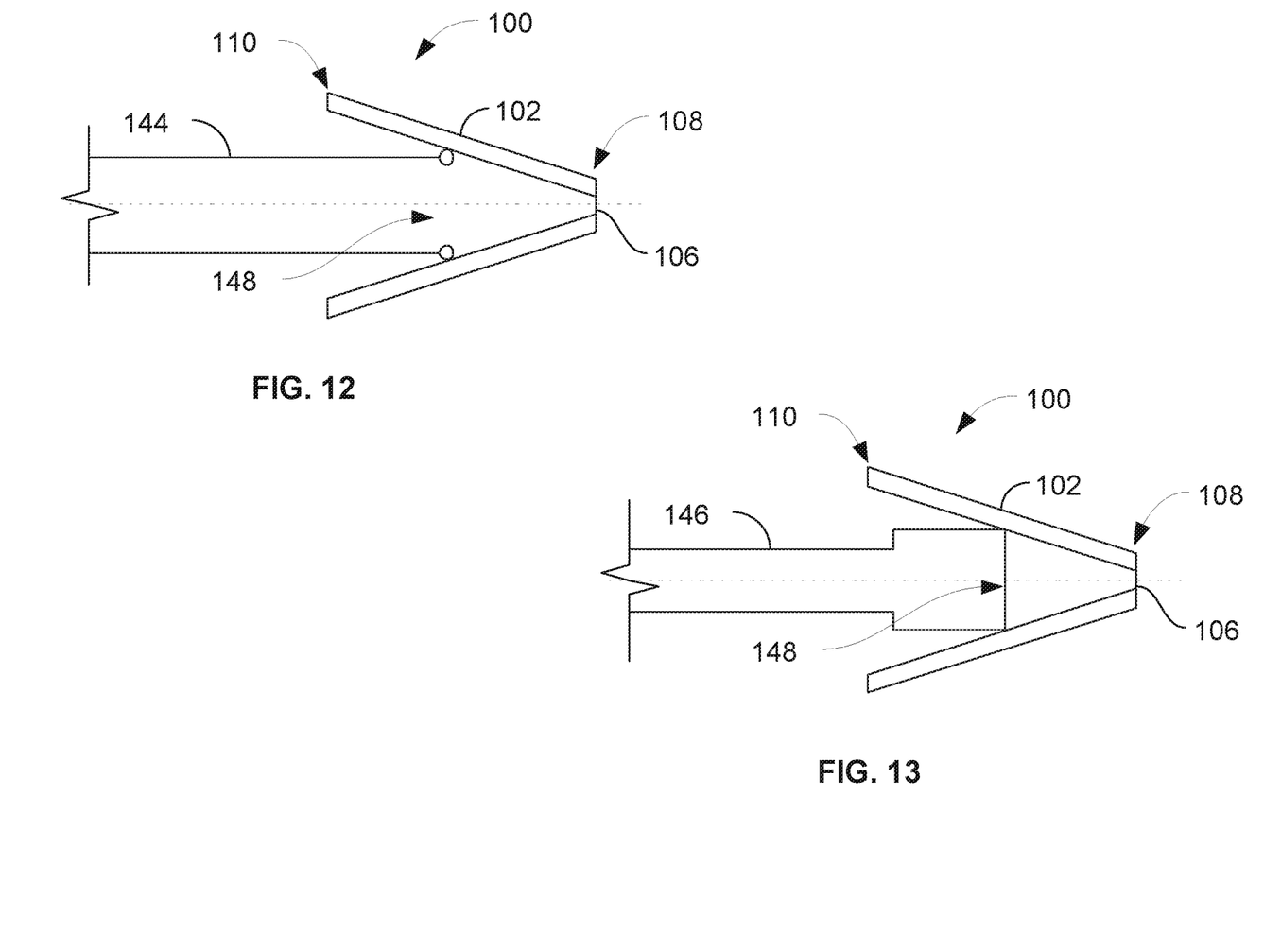
FIG. 12 illustrates a side cross-sectional view of a catheter tip with a ring-shaped stiff frame, according to an example embodiment.
FIG. 13 illustrates a side cross-sectional view of a catheter tip with a longitudinal stiff frame, according to an example embodiment.

FIGS. 12-13 illustrate other example catheter tips 100, according to various embodiments. In particular, FIG. 12 illustrates a catheter tip 100 with a ring-shaped stiff frame 144, while FIG. 13 illustrates a catheter tip 100 with a longitudinal stiff frame 146. As shown in FIGS. 12-13, the catheter tip 100 may include a flexible housing 102 that is conical in shape. The flexible housing 102 comprises a cavity 104 extending between an expandable opening 106 arranged at a first end 108 of the catheter tip 100 and a second end 110 of the catheter tip 100. Further, the catheter tip 100 may include a stiff frame 144, 146 disposed within the cavity 104 between the first end 108 and the second end 110 of the catheter tip 100. As shown in FIGS. 12-13, the stiff frames 144, 146 each define a lumen 148 that has a fixed diameter larger than a first diameter of the expandable opening 106 of the flexible housing 102, when the housing 102 is in an unflexed condition. The expandable opening 106 has a second diameter that is larger than the first diameter when the flexible housing 102 is in a flexed condition. In one example, the catheter tip 100 may transition from the unflexed condition to the flexed condition by application of a force applied to the second end 110 of the catheter tip 100 in a direction towards the centerline 149 of the catheter tip 100. In another example, the catheter tip 100 may transition from the unflexed condition to the flexed condition by a sliding movement of the first end 108 of the catheter tip 100 towards the lumen 148 in the stiff frame 144, 146 to retract the catheter tip 100 relative to the frame 144, 146.

In one example, the flexible housing 102 and the stiff frame 130, 144, 146 may be coupled to one another via a track. The track may ensure that the stiff frame 130 and the flexible housing 102 remain in contact, but enables the flexible housing 102 to slidably move relative to the stiff frame 130 to thereby move from the first position to the second position. Such a track may include a t-shaped member coupled to the flexible housing that fits into a corresponding t-shaped opening in the stiff frame 130, 144, 146. Other arrangements are possible as well.

Figure 14:
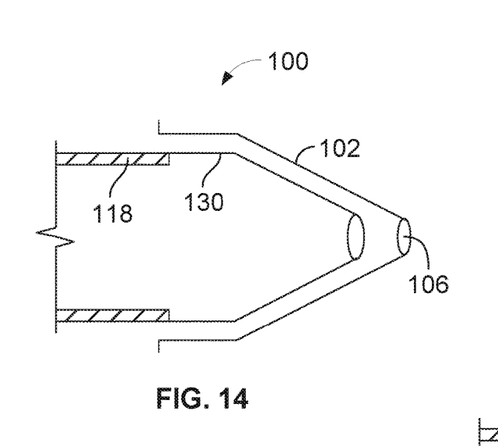
FIG. 14 illustrates a side cross-sectional view of a catheter tip in a first position, according to an example embodiment.
Figure 15:
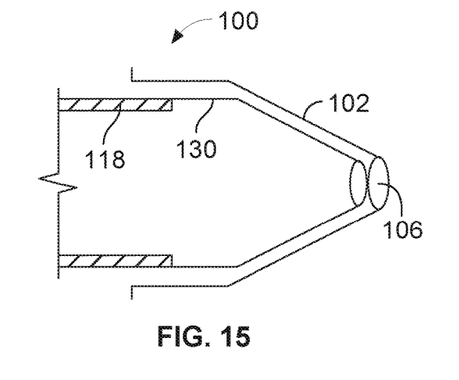
FIG. 15 illustrates a side cross-sectional view of the catheter tip of the example embodiment shown in FIG. 14 in a second position.

FIGS. 14 and 15 illustrate a catheter 118 coupled of a catheter tip 100 arranged such that the flexible housing 102 can be retracted so as to expand the expandable opening 106 of the catheter tip 100. In particular, FIGS. 14-15 show a catheter tip 100 that is flexible in such a way that the flexible housing 102 conforms to the outer surface of the stiff frame 130 and catheter 118 when retracted so as to allow a guidewire to be passed therethrough and minimize the crossing profile of the catheter 118 and catheter tip 100.

Figure 16:
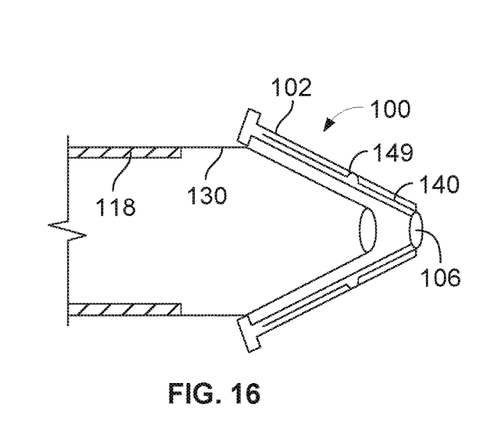
FIG. 16 illustrates a side cross-sectional view of a catheter tip including a pre-formed curvature in a first position, according to an example embodiment.
Figure 17:
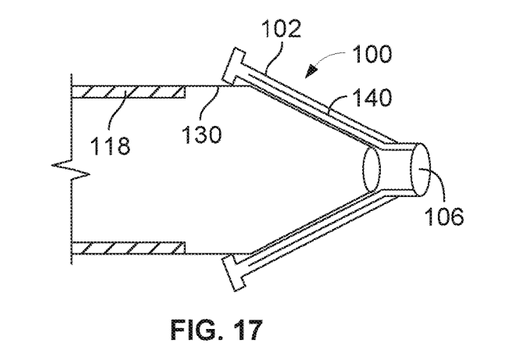
FIG. 17 illustrates a side cross-sectional view of the catheter tip of the example embodiment shown in FIG. 16 in a second position.
Figure 18:
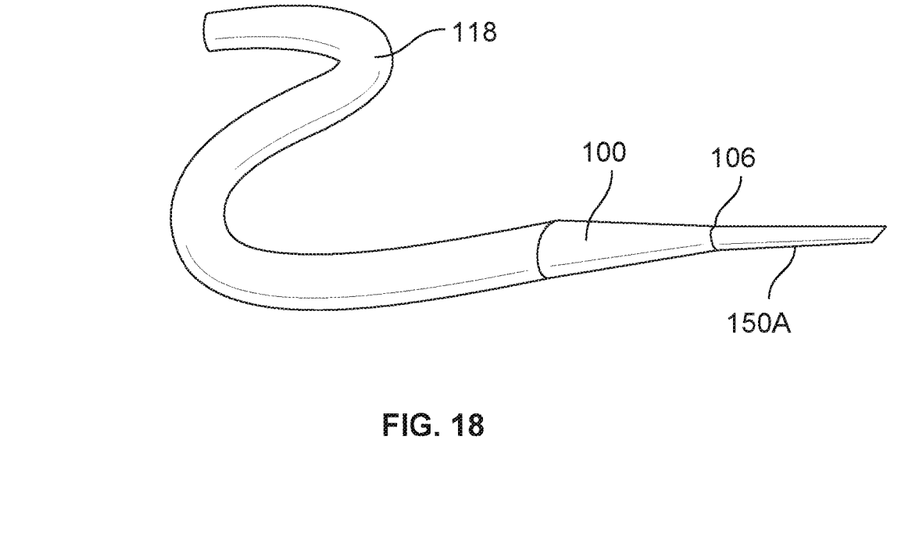
FIG. 18 illustrates a perspective view of a catheter coupled to an example catheter tip with a guidewire having a first diameter disposed therethrough, according to an example embodiment.
Figure 19:
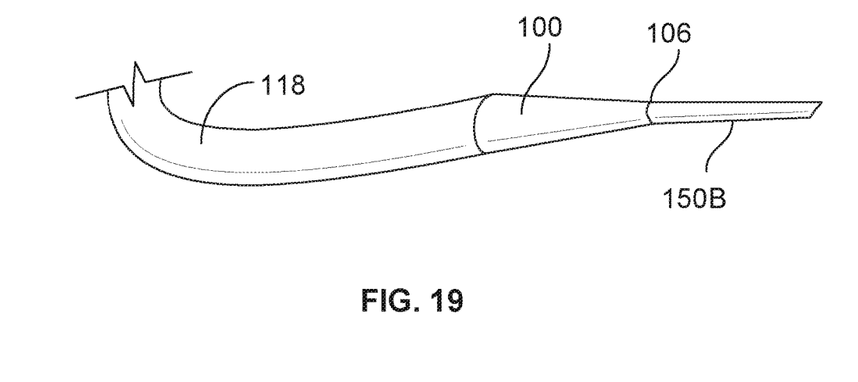
FIG. 19 illustrates a perspective view of the catheter coupled to the catheter tip of FIG. 18 with a guidewire having a second diameter disposed therethrough, according to an example embodiment.

FIGS. 16 and 17 illustrate a catheter 118 coupled to a catheter tip 100 having a flexible housing 102 that includes one or more stiff arms 140 with a pre-formed curvature 149 along its length. In one example, the one or more stiff arms 140 may include a nitinol frame embedded within the flexible housing 102. This pre-formed curvature 149 can be pinched in such a way that it flattens the stiff arm 140 effectually applying force so as to expand the expandable opening 106 of the catheter tip 100 allowing for a larger guidewire to be passed therein. FIG. 18 illustrates a catheter 118 coupled to an example catheter tip 100 with a guidewire 150A having a first diameter, according to an example embodiment. FIG. 19 illustrates a catheter 118 coupled to the example catheter tip 100 with a guidewire 150B having a second diameter, according to an example embodiment. As shown in FIGS. 18-19, the first diameter may be greater than the second diameter, such that the same catheter tip 100 may be used for guidewires 150A, B having different diameters and advantageously maintaining a seal about both guidewires 150A, B.

In operation, an example method may include (a) retracting the flexible housing 102 relative to the frame 130, 144, 146 of the catheter tip 100 according to the embodiments of FIGS. 8-17 from a first position to a second position, thereby increasing a first diameter of the expandable opening 106 to a second diameter, (b) positioning a guidewire 150 through the expandable opening 106, (c) advancing the flexible housing 102 from the second position to the first position, thereby decreasing the second diameter of the expandable opening 106, and (d) advancing the catheter tip 100 along the guidewire 150 to a target lumen. In another embodiment, the catheter tip 100 is coupled to a catheter 118 configured to have a guidewire-deployable device positioned within a lumen 120 of the catheter 118. In such an embodiment, the method may further include deploying the guidewire-deployable device from the lumen 120 of the catheter 118 into the target lumen.

In another example, the catheter tip 100 may not include the flexible housing 102. In such an example, the catheter tip 100 may include a plurality of pivotable arms 112 defining a cavity 104 extending between an expandable opening 106 arranged at a first end 108 of the catheter tip 100 and a second end 110 of the catheter tip 100. The plurality of pivotable arms 112 may be arranged to taper inwardly toward the cavity 104 at the first end 108. Such an embodiment may also include one or more pivots 114 arranged between an inner surface 116 of the plurality of pivotable arms 112 and the cavity 104.

In another such example where the catheter tip 100 does not include the flexible housing 102, the catheter tip 100 may include a plurality of stiff arms 140 defining a cavity 104 extending between an expandable opening 106 arranged at a first end 108 of the catheter tip 100 and a second end 110 of the catheter tip 100. In such an example, the plurality of stiff arms 140 may be arranged to taper inwardly toward the cavity 104 at the first end 108. Such an embodiment may further include a stiff frame 130 disposed within the cavity 104, where the plurality of stiff arms 140 are moveable relative to the stiff frame 130 from a first position in which an expandable opening 106 has a first diameter to the second position in which the expandable opening 106 has a second diameter that is larger than the first diameter. In the examples described above where the catheter tip 100 does not include the flexible housing 102, the first end 108 of the catheter tip 100 may include a valve or rubber flap to block blood flow from coming out of the catheter 118. Such a valve may include a one way valve, a check valve, or a diaphragm valve, as examples.

In operation, another example method may include (a) applying a force to the second end 107 of the catheter tip 100 according to any one of the embodiments described above thereby increasing a diameter of the expandable opening 106 at the first end 101 of the catheter tip 100, (b) positioning a guidewire 150 through the expandable opening 106, (c) removing the force from the second end 110 of the catheter tip 100 thereby decreasing the diameter of the expandable opening 106, and (d) advancing the catheter tip 100 along the guidewire 150 to a target lumen. In another embodiment, the catheter tip 100 is coupled to a catheter 118 configured to have a guidewire-deployable device positioned within a lumen 120 of the catheter 118. In such an embodiment, the method may further include deploying the guidewire-deployable device from the lumen 120 of the catheter 118 into the target lumen.

It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

The invention claimed is:
1. A catheter tip, comprising:
a plurality of pivotable arms defining a cavity extending between an expandable opening arranged at a first end of the catheter tip and a second end of the catheter tip, wherein the plurality of pivotable arms are arranged to taper inwardly toward the cavity at the first end; and one or more pivots arranged between an inner surface of the plurality of pivotable arms and the cavity and further arranged between the first end of the catheter tip and the second end of the catheter tip, wherein the expandable opening is configured to increase in diameter from a first position to a second position in response to application of an external force applied directly to an exterior surface of the second end of the catheter tip, wherein the external force is configured to be applied by pinching the exterior surface of the second end of the catheter tip in a direction towards a centerline of the catheter tip, wherein the one or more pivots comprise pivot points about which the plurality of pivotable arms rotate as the expandable opening transitions from the first position to the second position, and wherein the expandable opening is configured to provide a fluid tight seal around a guidewire in the first position.

2. The catheter tip of claim 1, wherein the plurality of pivotable arms are cone-shaped when the expandable opening is in the first position.

3. The catheter tip of claim 1, wherein the expandable opening has a diameter in the first position of between about 0.2032 mm to about 0.3556 mm.

4. The catheter tip of claim 1, wherein the expandable opening has a diameter in the second position ranging from about 0.2286 mm to about 1.016 mm.

5. The catheter tip of claim 1, further comprising a catheter coupled to the catheter tip.

6. The catheter tip of claim 5, further comprising a guidwire deployable device positioned within a lumen of the catheter, wherein the guidewire deployable device includes one of an occluder, a pacemaker lead, a snare or a stent graft positioned within a lumen of the catheter.

7. The catheter tip of claim 1, wherein the one or more pivots comprise a single ring, a discontinuous ring, a plurality of ball bearings, and/or a plurality of short shafts.

8. The catheter tip of claim 1, wherein the expandable opening comprises a single ring or a discontinuous ring defined by the plurality of pivotable arms at the first end of the catheter tip.

9. The catheter tip of claim 1, further comprising a plurality of biasing arms positioned between the cavity and the plurality of pivotable arms, wherein the plurality of biasing arms extend between the second end and the one or more pivots and are arranged to taper outwardly away from the cavity to the one or more pivots.

10. The catheter tip of claim 9, wherein each of the plurality of biasing arms is coupled at one end to a corresponding pivotable arm of the plurality of pivotable arms.

11. The catheter tip of claim 1, further comprising a biasing element positioned between the second end and the one or more pivots and arranged to bias the plurality of pivotable arms outwardly away from the cavity at the second end of the catheter tip and inwardly towards the cavity at the first end of the catheter tip.

12. The catheter tip of claim 11, wherein the biasing element is embedded in a flexible housing.

13. The catheter tip of claim 1, wherein the plurality of pivotable arms comprises exactly three pivotable arms.

14. The catheter tip of claim 1, wherein the plurality of pivotable arms are embedded in a flexible housing.

15. The catheter tip of claim 1, wherein the plurality of pivotable arms at the first end of the catheter tip include a plurality of ridges or teeth.

16. The catheter tip of claim 1, wherein the one or more pivots are embedded in a flexible housing.

17. A method comprising:
applying a force to the second end of the catheter tip according to claim 1 when the catheter tip is external to a body of a patient, thereby increasing a diameter of the expandable opening at the first end of the catheter tip;
positioning a guidewire through the expandable opening;
removing the force from the second end of the catheter tip thereby decreasing the diameter of the expandable opening; and
advancing the catheter tip along the guidewire to a target lumen in the patient.

18. The method of claim 17, wherein the catheter tip is coupled to a catheter with a stent graft positioned within a lumen of the catheter, the method further comprising:
deploying the stent graft from the lumen of the catheter into the target lumen.

* * * * *